United States Patent [19]

Nelson et al.

[11] Patent Number: 5,795,615
[45] Date of Patent: *Aug. 18, 1998

[54] PROCESS FOR PRODUCING METAL CARBOXYLATES FOR USE AS ANIMAL FEED SUPPLEMENTS

[75] Inventors: Christopher E. Nelson; Douglas Howard Catron, both of Des Moines, Iowa

[73] Assignee: Kemin Industries, Inc.

[*] Notice: The term of this patent shall not extend beyond the expiration date of Pat. No. 5,591,878.

[21] Appl. No.: 524,351

[22] Filed: Sep. 6, 1995

Related U.S. Application Data

[63] Continuation-in-part of Ser. No. 315,557, Sep. 30, 1994, abandoned.

[51] Int. Cl.$^6$ ............................ A23K 1/16; A23L 1/30
[52] U.S. Cl. .................... 426/648; 426/807; 556/114; 556/131
[58] Field of Search ........................ 426/635, 648, 426/806, 807; 556/114, 131

[56] References Cited

U.S. PATENT DOCUMENTS

| | | | |
|---|---|---|---|
| 2,452,003 | 10/1948 | Weber et al. | 556/131 |
| 3,755,391 | 8/1973 | Bertrand et al. | |
| 3,957,598 | 5/1976 | Merkl | 556/131 X |
| 4,060,535 | 11/1977 | Cinco | 556/114 X |
| 4,101,567 | 7/1978 | Fitzmaurice et al. | |
| 4,278,610 | 7/1981 | Maurer et al. | 556/131 X |
| 4,315,927 | 2/1982 | Evans | 424/245 |
| 4,636,572 | 1/1987 | Hudson et al. | |
| 4,700,000 | 10/1987 | Merkel et al. | 562/606 |
| 4,851,153 | 7/1989 | Kono et al. | 252/518 |
| 5,453,277 | 9/1995 | McCoy | 424/408 |
| 5,591,878 | 1/1997 | Nelson et al. | 556/49 |

FOREIGN PATENT DOCUMENTS 42-13764  8/1967  Japan .................... 556/114

OTHER PUBLICATIONS

*Organic Chemistry*, Kemp & Vellacio, eds., Worth Publishers, Inc. (New York: 1980), pp. 262–263.
P. 891 of *Organic Chemistry*, McMurray, ed., Brooks/Cole Publishing Co., Monterey, California, (1984).
*Introduction to Organic Chemistry*, 2$^{nd}$ Ed., Streitwieser, Jr. et al., eds., Macmillan Publishing Co., Inc. (New York: 1981), pp. 909–910.
The *Chemistry of Organic Compounds*, 2$^{nd}$ Ed., Noller, ed., W.B. Saunders Co., Philadephia, (1957), p. 370.
*CRC Handbook of Chemistry and Physics*, 55$^{th}$ Ed., Weast, ed. CRC Press, Cleveland, Ohio (1974) pp. 122–125.

*Primary Examiner*—Arthur L. Corbin
*Attorney, Agent, or Firm*—Welsh & Katz, Ltd.

[57] ABSTRACT

A process for producing divalent metal carboxylates having the formula, $M(CH_3(CH_2)_xCOO^-)_2$, wherein M is the divalent metal cation, zinc ($Zn^{+2}$) or copper ($Cu^{+2}$) and x is zero or 1 is disclosed. In this process, an anhydrous $C_2$–$C_3$ carboxylic acid is admixed with a basic divalent metal compound that is an oxide, hydroxide or carbonate of $Zn^{+2}$ or $Cu^{+2}$ in the absence of added solvent or other diluent. The divalent metal carboxylate so produced is used as a biologically available and economical source of trace metals for supplementation in animal diets.

15 Claims, No Drawings

PROCESS FOR PRODUCING METAL CARBOXYLATES FOR USE AS ANIMAL FEED SUPPLEMENTS

CROSS-REFERENCE TO RELATED APPLICATION

This is a continuation-in-part of application Ser. No. 08/315,557, filed Sep. 30, 1994, now abandoned which disclosure is incorporated herein by reference.

DESCRIPTION

1. Technical Field

The present invention relates to a process for producing metal carboxylates, and more particularly divalent metal acetate and propionate salts that are used for trace metal supplementation of animal feed.

2. Background of the Invention

Trace elements are essential for the nutrition of animals, playing important roles in many biochemical and physiological processes. These elements include metals that form divalent cations such as zinc, copper, iron, manganese, cobalt, chromium, and molybdenum. All but molybdenum have been shown to be deficient in some natural feed ingredients, necessitating the use of supplements to make the diet nutritionally complete.

Several chemical forms of trace metals are available for supplementation of animal diets including the inorganic salts of the trace metal, metal-amino acid complexes, metal-amino acid chelate complexes, metal-proteinate complexes, and metal-polysaccharide complexes (Official Publication of American Feed Control Officials, 1995, pages 209–210). U.S. Pat. No. 4,315,927 also discloses the use of a metal carboxylate complex, zinc picolinate, as a food supplement for both humans and other animals. All of the complexes result from the complexing of a soluble metal salt with the amino acid, chelate, proteinate, polysaccharide, or carboxylic acid.

The salts of acetic acid, zinc acetate, manganese acetate, and cobalt acetate, have been approved for use as animal feed supplements (21 CFR 582.80). Zinc acetate is usually prepared in a conventional manner as is discussed below.

U.S. Pat. No. 4,700,000 discloses that carboxylic acid salts are conventionally synthesized by reacting a carbonate, hydroxide, or oxide with a concentrated or dilute carboxylic acid. The carboxylic acid is in solution as denoted by the terms "concentrated" and "dilute". The carbonate, hydroxide, or oxide are typically aqueous bases (soluble metal salts) that are reacted with the carboxylic acid to form a carboxylic acid salt. Sulfates, chlorides, and nitrates can also be used. The reactants in the conventional method are therefore in an aqueous solution.

U.S. Pat. No. 4,700,000 also discloses that calcium propionate is prepared by reacting propionic acid with calcium hydroxide in an aqueous solution. After concentration and crystallization, the product is separated from the solution by filtration, decantation, or centrifugation, dried and ground. U.S. Pat. No. 4,315,927 discloses that zinc picolinate is prepared by adding picolinic acid to an aqueous solution of a water-soluble metal salt, zinc sulfate. The product is precipitated, purified by recrystallization, recovered and dried by freeze-drying.

A disadvantage of synthesis in an aqueous medium is that the use of an aqueous solution necessitates the separation of the precipitated product from the solution, and drying of the recovered product. Another disadvantage of a conventional method is that in some cases, the divalent metal-containing base is sparingly soluble or insoluble in water.

BRIEF SUMMARY OF THE INVENTION

The present invention relates to an efficient and economical process for producing a divalent metal salt of a $C_2$–$C_3$ carboxylic acid; i.e., a metal carboxylate. Specifically, divalent metal acetates and divalent metal propionates are contemplated, and preferably divalent metal propionates. The divalent metal $C_2$–$C_3$ carboxylates have the formula, $M(CH_3(CH_2)_xCOO^-)_2$, wherein M is the divalent metal cation, zinc ($Zn^{+2}$) or copper ($Cu^{+2}$) and x is zero or 1. Thus, zinc acetate or proprionate and copper(II) acetate or propionate are contemplated.

The process involves agitatingly admixing anhydrous propionic acid or acetic acid with an approximately stoichiometric amount of a dry, basic divalent metal compound that is an oxide, hydroxide or carbonate of $Zn^{+2}$ or $Cu^{+2}$ to form an exothermic reaction mixture. This admixture is carried out in the absence of added solvent or other diluent. The exothermic reaction mixture so formed produces water as a product and a corresponding divalent metal propionate or acetate. Carbon dioxide is also formed when zinc or copper (II) carbonate are used. That exothermic reaction mixture is maintained with agitation while continually removing the formed water to form the divalent metal cation propionate or acetate in dry, preferably particulate, form.

An advantage of this invention is that it provides a process of making divalent metal carboxylates that is low in cost and easy to perform on a large commercial scale. Another advantage is that preparation of the divalent metal carboxylate requires relatively little input of energy. Still further advantages of the invention will be apparent to a worker of ordinary skill from the description that follows.

DETAILED DESCRIPTION OF THE INVENTION

The present invention relates to the preparation of divalent metal propionates and metal acetates. The divalent metal $C_2$–$C_3$ carboxylates have the formula $M(CH_3(CH_2)_xCOO^-)_2$ wherein M is the divalent metal cation that is zinc ($Zn^{+2}$) or copper ($Cu^{+2}$) and x is zero or 1. The source of the metal cation, M, is a basic metal compound that is an oxide, hydroxide or carbonate preferably zinc oxide and copper(II) carbonate.

The following description of the present invention illustrates a process of preparing zinc propionate and copper(II) propionate using propionic acid, but the description is equally useful for the preparation of zinc acetate and copper acetate using acetic acid.

Zinc propionate or copper propionate is prepared by admixing anhydrous propionic acid with a dry, basic divalent metal compound that is a carbonate, hydroxide, or oxide of zinc or copper(II), preferably zinc oxide or copper carbonate. The reaction unexpectedly occurs without having to dissolve the propionic acid or the basic divalent metal compound in water or another added solvent, or to suspend the reactants in any other added liquid or solid diluent. This is an advantage because the basic metal compounds used in the present invention are sparingly soluble in water.

The propionic acid and the basic divalent metal compound are used in approximately stoichiometric amounts, with the propionic acid preferably being in slight excess, e.g., up to about 0.5 moles. The desired molar ratio of propionic acid to the basic divalent metal compound for the divalent cations, copper and zinc, is within the range of about 1.5:1 to about 2.5:1, preferably about 2:1, which is stoichoimetric.

When used in the reaction, both the propionic acid and basic divalent metal compound are anhydrous. That is, both are substantially free of water so that neither contains more than a total of about 5 weight percent water or an aggregate of about 10 weight percent water. Preferably, the propionic acid (or acetic acid) contains less than about 0.5 weight percent water. More preferably, the propionic acid (or acetic acid) contains at most about 0.1 to about 0.2 weight percent water. The basic metal compound preferably has no waters of crystallization, as is the case with the usually reported and available forms of those basic metal compounds.

The admixed basic, divalent metal compound and propionic acid (acetic acid) are agitated together and form an exothermic reaction mixture whose components react to produce water and the copper(II) or zinc carboxylate. The exothermic reaction mixture so prepared is maintained with agitation while the water that is formed is continually removed so that the divalent metal cation propionate (acetate) that is formed is dry and free of water as discussed before.

The basic divalent metal compound is utilized in a dry, particulate form. The use of a relatively small particle size is preferred to help assure contact of the reactants and subsequent reaction. Thus, a powder form is preferred, although particles can be used that are sized to pass through at least a No. 3 sieve, U.S. Standard Sieve Series (about ¼-inch opening), with no smallest sized particle being contemplated other than for the convenience of the user. Use of a high shear mixer also helps to assure that the basic metal compound particles are broken to an appropriate size.

Propionic acid melts at about −23° to −24° C. and boils at about 142° C. (about 288° F.) at one atmosphere. The propionic acid is utilized in its liquid form. Propionic acid forms an azeotrope with water that boils at about 100° C. (about 212° F.) and contains about 18 weight percent propionic acid. As a consequence of the formation of the azeotrope and the relatively low boiling point of that mixture, some propionic acid can be and is lost at higher reaction temperatures as water is removed from the reaction mixture. Acetic acid melts at about 17° C. and boils at about 118° C. at one atmosphere. Acetic acid forms an azeotrope with water that boils at about 77° C. and contains about 3 weight percent acetic acid.

The reactants, either the $C_2$–$C_3$ carboxylic acid or the basic metal compound or both, can be preheated relative to ambient temperature (20° C.) to a temperature within the range of about 25° C. to about 100° C., and preferably about 30° to about 60° C. In one preferred embodiment the $C_2$–$C_3$ carboxylic acid or basic metal compound such as zinc oxide or both are preheated to a temperature within the range of about 30° to about 50° C., more preferably to about 40° C. However, such heating has been found to be unnecessary during large-scale production.

The anhydrous propionic acid is added to the dry basic metal compound in a mixing apparatus. Any reaction vessel and mixer can be used. In a laboratory procedure a beaker can be used as the mixing vessel with a stirring rod as a mixer. However, for larger scale preparations, a high shear mixing apparatus is preferred, and it is more preferred to use a high shear plow mixer. Exemplary plow mixers include the Littleford™ brand mixer (Littleford Bros. Inc.) and the Marion™ brand mixer (Marion Mixer Co., Marion, Iowa, *Perry's Chemical Engineer's Handbook*, 6th ed., Perry et al., eds., McGraw-Hill Inc., New York, 1984, page 19–18) equipped with plow-shaped and high-shear mixing blades for turbulent mixing. Additional suitable mixers can also be found in Chapter 19 of the text by Perry et al. After thorough mixing (agitation with shear), the reaction is typically completed within minutes, but can be an hour or longer at lower temperatures as where the exotherm created by the acid base reaction is cooled.

The rate and temperature of reaction are governed by a number of variables such as the prereaction temperature of the reactants, the agitation rate within the reactor, the particle size of the basic metal compound, and the rate at which propionic acid is admixed into the reaction mixture. It is preferred to carry out the reaction at a temperature between about 150° and about 20° F. (about 65° to about 93° C.).

The reaction proceeds exothermically according to the following equations:

1) $ZnO + 2CH_3CH_2COOH \longrightarrow Zn(CH_3CH_2CO_2)_2 + H_2O$

2) $CuCO_3Cu(OH)_2 + 4CH_3CH_2COOH \longrightarrow 2Cu(CH_3CH_2CO_2)_2 + 3H_2O + CO_2$

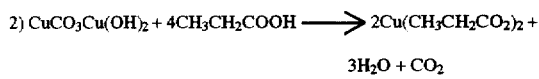

Water and heat are generated when propionic acid and the basic metal compound are reacted, as is carbon dioxide when a carbonate is used. The water along with some propionic acid is continually removed from the reaction mixture.

In the preparation of zinc propionate, the heat of the reaction is sufficient to evaporate the water formed. In the preparation of copper propionate, additional heat is added.

The water is preferably released as vapor that can be aspirated under reduced pressure conditions from the exothermic reaction mixture. A well-insulated mixer is preferably employed to capture the heat given off in the exothermic reaction and evaporate water from the product. The resulting product is dry and particulate.

In one embodiment of the present invention, anhydrous propionic acid was mixed with dry zinc oxide to yield greater than 90 percent zinc propionate. The resulting zinc propionate was a white powder, and was in a form readily utilizable for dietary supplementation. Unlike the conventional aqueous method of preparation, the product is not precipitated and then separated from solution. Moreover, no drying of the product by vacuum desiccation, spray drying or freeze drying is required, thereby saving energy costs. In comparison, using the conventional method where the zinc oxide was dissolved in an aqueous solution of propionic acid, and the solution was heated to boiling and evaporated to yield zinc propionate crystals, the yield of zinc propionate was 75.2 percent, after two crystallizations and drying under reduced pressure for 16 hours.

The divalent metal propionate so prepared is dry (substantially free from water, as before) and particulate. It is typically and preferably a powder that is itself dry but can clump slightly due to the presence of a small amount of unreacted acid. It is most preferred that the divalent metal propionate have an appearance similar to that of commercially available talcum powder. That material can be used as such, but is typically recovered and packaged for sale to others. Recovery techniques are those normally used for non-toxic or slightly toxic powders. Purities and yields of about 80 percent and above are typically obtained, with purities and yields in excess of 90 percent being usual and preferred.

EXAMPLE 1

Zinc Propionate

Two preparations of zinc propionate were made by combining 81 grams of zinc oxide and 148 grams of propionic acid in heavy-walled glass beakers. This resulted in a relative molar ratio of 1:2 of zinc cation to propionic acid. The beakers were used to insulate the reaction. One preparation utilized reactants preheated to 100° F. (38° C.), whereas the second preparation started at room temperature. The reactants were rapidly mixed with a stirring rod. The resulting vapor was permitted to escape from the reaction beaker. After mixing for eight minutes, a white powdery material was formed. Greater than 90 percent zinc propionate was obtained for the preheated reactants and 80 percent zinc propionate for the reactants at room temperature.

EXAMPLE 2

Copper Propionate

A preparation of copper propionate is made by combining 221 grams of copper carbonate and 296 grams of propionic acid as in Example 1. This results in a relative molar ratio of 1:2 of copper(II) cation to propionic acid. The reaction is run at room temperature. The reactants are rapidly mixed with a stirring rod. The copper carbonate reacts readily with the propionic acid. Carbon dioxide is generated along with water and heat. The resulting copper propionate is a blue-green powder.

EXAMPLE 3

Zinc Acetate

A preparation of zinc acetate is made by combining 81.38 grams of zinc oxide and 60.05 grams of acetic acid as in Example 1. The zinc oxide reacts exothermically with the acetic acid to produce zinc acetate.

EXAMPLE 4

Copper Acetate

A preparation of copper acetate is made by combining 221 grams copper carbonate and 120 grams of acetic acid as in Example 1. The copper carbonate reacts exothermically with acetic acid to produce copper acetate.

EXAMPLE 5

Zinc Propionate: Pilot Scale

Five batches of zinc propionate, 200 pounds each, were prepared using a Marion brand mixer supplied by the Marion Mixer Company, Marion, Iowa. The mixer was equipped with high-shear mixing blades set at right angles to the primary plow mixing blades. The high-shear blades were operated at a fixed speed of 3,500 rpm and the primary mixing blades were operated at 40 rpm.

The initial temperature of the zinc oxide and propionic acid were varied, as was the time at which the high-shear blades were engaged. Vent stack temperatures approximately six inches from the top of the mixer were monitored as a measure of the rate of reaction. Each batch was prepared by charging the mixer with 77 pounds of zinc oxide followed by spraying the dry zinc oxide with 140 pounds of propionic acid at nine pounds per minute. Starting material temperatures and the time at which the high-shear mixing blades ("choppers") were engaged are summarized below in Table 1.

TABLE 1

Parameters for Pilot Scale Production of Zinc Propionate in a High-Shear Mixer

| Batch | Temperature Propionic Acid | Zinc Oxide | Choppers |
|---|---|---|---|
| MMZNP-1 | 100° F. | Ambient | None |
| MMZNP-2 | 100° F. | Ambient | After all propionic acid |
| MMZNP-3 | 100° F. | Ambient | After 25 percent of propionic added |
| MMZNP-4 | Ambient | 100° F. | After 25 percent of propionic added |
| MMZNP-5 | 100° F. | 100° F. | After 25 percent of propionic added |

Five samples, 150 g each, were taken at random from each preparation. A composite sample comprising 5 g from each sample was prepared from each preparation for analysis.

Within 48 hours of production, each pilot preparation was analyzed for yield using the above samples. Approximately ten grams of each of the above composites were weighed into a tared fritted glass funnel of 10–15µ pore size. Sample weights were recorded to two decimal places. In each funnel, 25 mL of hexane were added and the sample stirred for one minute. The hexane was filtered off under reduced pressure, and the procedure repeated twice more. Each sample was then extracted once with 25 mL of dry acetone to remove residual hexane. Thereafter, 50 mL of water were added to each funnel and slurried with the sample for one minute. The water was then removed under reduced pressure filtration and the extraction repeated twice more for a total of 150 mL of extraction water. The residue was then extracted with 25 mL of acetone to remove residual water, then 25 mL of petroleum ether to remove excess acetone. The residue was then air-dried in the funnel under reduced pressure for 15 minutes. The final material was carefully removed from the funnel and weighed. Weights were recorded to two decimal places. Net conversion was calculated by subtracting the ratio of final residue weight to initial composite sample from one. Results of this analysis and physical description of pilot scale product are shown in Table 2.

TABLE 2

Conversion Analysis Results and Description of Pilot Scale Zinc Propionate

| Batch | Initial Weight (g) | Final Weight (g) | Purity of ZnP* | Appearance |
|---|---|---|---|---|
| MMZNP-1 | 10.15 | 1.25 | 87.7% | White, poorly flowing powder, hard clumps 2–20 mm |
| MMZNP-2 | 10.16 | 0.91 | 91.0% | White, poorly flowing powder, soft clumps 2–12 mm |
| MMZNP-3 | 10.18 | 0.64 | 93.7% | White, poorly flowing powder, soft clumps 2–12 mm |
| MMZNP-4 | 10.79 | 0.85 | 92.1% | White, poorly flowing powder, soft clumps 2–12 mm |

TABLE 2-continued

Conversion Analysis Results and Description of Pilot Scale Zinc Propionate

| Batch | Initial Weight (g) | Final Weight (g) | Purity of ZnP[a] | Appearance |
|---|---|---|---|---|
| MMZNP-5 | 10.11 | 0.99 | 90.2% | Fine, flowing white powder, minimal clumps |
| ZnPr-P&B[b] | 10.06 | 0.41 | 95.9% | Fine, flowing white powder |
| ZnPr-MSF[b] | 9.82 | 0.01 | 99.9% | Fine, flat white crystals |
| ZnO | 9.95 | 9.89 | N/A | Fine, flowing white powder |

[a]ZnP = Zinc propionate. Based on residual solids. Not corrected for zinc oxide residual solids.
[b]P & B = Purchased from Pfaltz & Bauer; MSF = prepared at Kemin Industries, by reaction in dilute aqueous solution, concentration and crystallization.

As can be seen, purity of the zinc propionate product exceeded 90 percent in every case in which the high-shear mixing blades were used during production. The best overall purity was obtained using pre-heated propionic acid and engaging the choppers after about 25 percent of the acid had been added to the mixer. However, there was little difference to be seen between this and pre-heating the zinc oxide prior to propionic acid addition. Although the lowest yield was obtained by pre-heating both reactants (MMZNP-5), this product was the only one that was substantially free of clumps and free-flowing immediately after production.

When assayed by the residual solids method, zinc oxide itself showed a 0.6 percent loss in weight. Based on the appearance of the filtrate, this is due to fine (<10 micron) particles and the presence of zinc hydroxide. Zinc oxide itself is soluble to only 0.00016 g/100 ml water. The zinc oxide used in this study was not less than 95 percent pure.

For the most part, stack temperatures reached 160° F. and remained between 150° F. and 200° F. In particular, MMZNP-5 reached a stack temperature of 240° F., and appeared likely to go higher.

As was noted before, propionic acid forms an azeotrope with water with a boiling point of about 188° F. Thus, the portions of the stack gases at stack temperatures for MMZNP-2, 3, 4 and 5 above 160° F. almost certainly represent at least some azeotropic loss of propionic acid from the system along with water generated by the zinc oxide-propionic acid reaction. It is believed that loss of propionic acid accounts for both the lower purity and dry, dusty appearance of the zinc propionate in MMZNP-5.

The reaction time was no less than 70 minutes for batches MMZNP 2-5 and 90 minutes for MMZNP-1.

EXAMPLE 6

Comparative Zinc Bioavailability

A study was conducted to compare the relative biological availability of zinc propionate, zinc methionine and zinc sulfate. The zinc preparations were added to the basal feed of day-old broilers at the levels indicated in Table 3. Each zinc treatment was replicated eight times and each pen contained ten male birds.

TABLE 3

Design of Zinc Bioavailability Trial

| Treatment z ID | Source | Level mg/kg | Pen | | | | | | | |
|---|---|---|---|---|---|---|---|---|---|---|
| 1 | Zinc Propionate | 10 | 13 | 8 | 21 | 22 | 35 | 30 | 49 | 68 |
| 2 | Zinc Propionate | 20 | 25 | 20 | 33 | 16 | 5 | 18 | 67 | 56 |
| 3 | Zinpro ® | 10 | 1 | 14 | 3 | 34 | 29 | 12 | 79 | 86 |
| 4 | Zinpro ® | 20 | 31 | 2 | 9 | 46 | 17 | 48 | 55 | 74 |
| 5 | Zinc sulfate | 0 | 37 | 44 | 27 | 10 | 23 | 36 | 91 | 50 |
| 6 | Zinc sulfate | 10 | 19 | 38 | 15 | 28 | 47 | 42 | 73 | 92 |
| 7 | Zinc sulfate | 20 | 43 | 32 | 45 | 40 | 11 | 24 | 85 | 62 |
| 9 | Zinc sulfate | 30 | 7 | 26 | 39 | 4 | 41 | 6 | 61 | 80 |

Zinpro ® = Zinc methionine bisulfate; Zinpro Corporation, Minneapolis, MN.

Basal feeds and zinc compound were mixed in a horizontal feed mixer providing the desired ingredient composition as shown in Table 4. The broilers were fed the rations for 21 days. Feed weights were taken during the trial. Body weights were measured at the beginning and at the end of the trial. On day 21, zinc levels in the blood and tibia ash were determined. The assay procedures for total tibia zinc content or concentration to assess zinc utilization are similar to those used by Wedekind et al., *J. Anim. Sci.*, 70:178–187 (1992). The data were analyzed according to the SAS statistical package.

TABLE 4

Formulation and Approximate Analysis of Basal Feed

| Ingredient | Percent |
|---|---|
| Corn yellow | 57.060 |
| Soybean meal - 48% | 34.621 |
| Fat | 3.096 |
| DL methionine[1] | 2.339 |
| Salt | 0.289 |
| Limestone | 0.621 |
| Defluorinated phosphate | 1.724 |
| Vitamin premix | 0.050 |
| Trace min. premix[2] | 0.050 |
| Biocox[3] | 0.100 |
| Bacitracin MD-50[4] | 0.050 |

[1]DL methionine is used to equalize methionine in all ratios.
[2]Trace mineral premix does not contain zinc.
[3]Available from Hoffmann-LaRoche, Inc., Nutley, NJ.
[4]Available from A.L. Laboratories, Ft. Lee, NJ.

Chick growth parameters and zinc levels in the blood and tibia ash were used as criteria to determine the biological availability of zinc. The broilers fed with zinc propionate had the same ending body weight as the broilers fed with zinc methionine at both the 10 mg/kg and 20 mg/kg levels. Both organic sources provided statistically significant higher ending body weights than did zinc sulfate at both the 10 mg/kg and 20 mg/kg levels. A similar set of results was seen for weight gain over the 21 day trial. Additionally, broilers fed with zinc propionate and zinc methionine showed comparable levels of zinc in the blood and tibia ash on day 21. With these data, a relative biological availability for zinc propionate and zinc methionine can be calculated. The summary of this calculation is shown in Table 5 below. The biological availability of zinc sulfate was arbitrarily set at 100%. For all parameters, there was no statistically significant difference between zinc propionate and zinc methionine with the exception of feed conversion. There was a slight advantage in the broilers treated with zinc propionate compared to zinc methionine. It can thus be concluded that zinc propionate showed equal biological availability and equal performance enhancement as zinc methionine.

TABLE 5

Relative Biological Availability (%)

| Criterion | Sulfate | Propionate | Zinpro ® |
|---|---|---|---|
| Ending body weight (lbs) 21 days | 100.00[b] | 128.21[a] | 132.46[a] |
| Body weight gain (lbs) 21 days | 100.00[b] | 128.24[a] | 131.52[a] |
| Feed conversion (corr.) 3–21 days | 100.00[a] | 100.30[a] | 90.38[b] |
| Bone ash (%) 21 days | 100.00[b] | 113.18[a] | 113.95[a] |
| Tibia ash zinc (µg/g) | 100.00[b] | 125.67[a] | 123.99[a] |
| Plasma Zinc (µg/ml) | 100.00[b] | 113.33[a] | 124.00[a] |

Note:
Means within a row grouping without a common superscript are significantly different ($P < 0.05$) as determined by Least Significant Difference.

The foregoing description and the examples are intended as illustrative and are not to be taken as limiting. Still other variations within the spirit and scope of this invention are possible and will readily present themselves to those skilled in the art.

We claim:

1. A process for preparing a dry, particulate metal carboxylate animal feed supplement having the formula $M(CH_3(CH_2)_xCOO^-)_2$, wherein M is a divalent metal cation that is zinc ($Zn^{+2}$) or copper(II) ($Cu^{+2}$) and x is zero or 1, that comprises the steps of:

(a) agitatingly admixing an anhydrous $C_2$–$C_3$ carboxylic acid with an approximately stoichiometric amount of a dry, particulate basic metal compound that is an oxide, hydroxide or carbonate of $Zn^{+2}$ or $Cu^{+2}$, said admixing being carried out in the absence of added solvent or other diluent to form an agitated exothermic reaction mixture that produces water as a product; and (b) maintaining said exothermic reaction mixture under agitation while continually removing said water for a time period sufficient to form zinc or copper(II) $C_2$–$C_3$ carboxylate in dry, particulate form.

2. The process of claim 1 including the further step of recovering the formed zinc or copper(II) carboxylate.

3. The process of claim 1 wherein the basic metal compound is zinc oxide.

4. The process of claim 1 wherein the basic metal compound is copper carbonate.

5. The process of claim 1 wherein said $C_2$–$C_3$ carboxylic acid is used in excess.

6. The process of claim 1 wherein said $C_2$–$C_3$ carboxylic acid is propionic acid.

7. The process of claim 1 wherein said $C_2$–$C_3$ carboxylic acid is acetic acid.

8. The process of claim 1 wherein the $C_2$–$C_3$ carboxylic acid and the basic metal compound are mixed together using a mixer with high-shear mixing blades.

9. A process for preparing a dry, particulate zinc or copper(II) propionate animal feed supplement that comprises the steps of:

(a) agitatingly admixing anhydrous propionic acid with an approximately stoichiometric amount of a dry, particulate basic metal compound that is an oxide, hydroxide or carbonate of zinc or copper(II), said admixing being carried in a mixer using high-shear mixing blades and in the absence of added solvent or diluent to form an agitated exothermic reaction mixture that produces water as a product;

(b) maintaining said exothermic reaction mixture under agitation while continually removing said water for a time period sufficient to form zinc propionate or copper (II) propionate in dry, particulate form; and (c) recovering said dry, particulate zinc propionate or copper propionate.

10. The process of claim 9 wherein the basic metal compound is zinc oxide.

11. The process of claim 9 wherein the basic metal compound is copper carbonate.

12. The process of claim 9 wherein said propionic acid is used in excess.

13. A process for preparing a dry, particulate metal carboxylate animal feed supplement having the formula $M(CH_3(CH_2)_xCOO^-)_2$, wherein M is a divalent metal cation that is zinc ($Zn^{+2}$) or copper(II) ($Cu^{+2}$) and x is zero or 1, that comprises the steps of:

(a) separately providing an anhydrous $C_2$–$C_3$ carboxylic acid and a dry, particulate basic metal compound that is an oxide, hydroxide or carbonate of $Zn^{+2}$ or $Cu^{+2}$, and heating the $C_2$–$C_3$ carboxylic acid or the basic metal compound or both the $C_2$–$C_3$ carboxylic acid and the basic metal compound to a temperature of about 25° to about 100° C. relative to ambient temperature prior to admixing;

(b) agitatingly admixing said anhydrous $C_2$–$C_3$ carboxylic acid with an approximately stoichiometric amount of said dry, particulate basic metal compound, said admixing being carried out in the absence of added solvent or other diluent, to form an agitated exothermic reaction mixture that produces water as a product; and (c) maintaining said exothermic reaction mixture under agitation while continually removing said water for a time period sufficient to form zinc or copper(II) $C_2$–$C_3$ carboxylate in dry, particulate form.

14. The process of claim 13 wherein the $C_2$–$C_3$ carboxylic acid is propionic acid, the basic metal compound is zinc oxide, and the propionic acid or the zinc oxide or both the propionic acid and the zinc oxide are heated within the range of about 30° to about 50° C. prior to admixing.

15. The process of claim 14 wherein the propionic acid or the zinc oxide or both the propionic acid and the zinc oxide are heated to about 40° C. prior to admixing.

* * * * *